(12) United States Patent
Villani et al.

(10) Patent No.: US 8,449,512 B2
(45) Date of Patent: May 28, 2013

(54) STOMA STABILITATING DEVICE AND METHOD

(75) Inventors: Mario Villani, Boylston, MA (US); Leo Cappabianca, Worcester, MA (US); David A. Merrill, Durham, NH (US); Rosanna Villani, Boylston, MA (US); Giuseppe Villani, Shrewsbury, MA (US)

(73) Assignee: DaVinci Biomedical Research Products Inc., South Lancaster, MA (US)

( * ) Notice: Subject to any disclaimer, the term of this patent is extended or adjusted under 35 U.S.C. 154(b) by 477 days.

(21) Appl. No.: 12/757,309

(22) Filed: Apr. 9, 2010

(65) Prior Publication Data

US 2011/0251452 A1    Oct. 13, 2011

(51) Int. Cl.
*A61F 5/44* (2006.01)

(52) U.S. Cl.
USPC .......... 604/332; 604/277; 604/278; 128/887; 623/1.12; 623/23.7

(58) Field of Classification Search
USPC .......... 604/332, 277, 278; 128/887; 623/1.12, 623/23.7
See application file for complete search history.

(56) References Cited

U.S. PATENT DOCUMENTS

| | | | |
|---|---|---|---|
| 3,021,843 A * | 2/1962 | Perry | 604/339 |
| 3,253,594 A * | 5/1966 | Matthews et al. | 604/103.03 |
| 3,752,162 A * | 8/1973 | Newash | 604/175 |
| 3,905,372 A * | 9/1975 | Denkinger | 604/359 |
| 4,359,051 A | 11/1982 | Oczkowski | |
| 4,429,424 A | 2/1984 | Waldner | |
| 4,474,182 A | 10/1984 | Rea et al. | |
| 4,505,976 A | 3/1985 | Doehnert et al. | |
| 4,534,761 A * | 8/1985 | Raible | 604/175 |
| 4,551,490 A | 11/1985 | Doyle et al. | |
| 4,555,242 A | 11/1985 | Saudagar | |
| 4,592,750 A | 6/1986 | Kay | |
| 4,596,566 A | 6/1986 | Kay | |
| 4,705,518 A * | 11/1987 | Baker et al. | 623/14.13 |
| 4,768,503 A | 9/1988 | Highgate et al. | |
| 4,790,810 A | 12/1988 | Pugh, Jr. et al. | |
| 4,854,316 A * | 8/1989 | Davis | 606/153 |
| 4,856,504 A * | 8/1989 | Yamamoto et al. | 606/59 |
| 4,915,694 A * | 4/1990 | Yamamoto et al. | 604/180 |
| 4,961,747 A | 10/1990 | Wascher et al. | |
| 5,004,454 A | 4/1991 | Beyar et al. | |
| 5,041,077 A | 8/1991 | Kulick | |
| 5,041,136 A | 8/1991 | Wascher et al. | |
| 5,109,843 A | 5/1992 | Melvin et al. | |
| 5,116,615 A | 5/1992 | Gokcen et al. | |
| 5,176,649 A * | 1/1993 | Wakabayashi | 604/164.09 |

(Continued)

*Primary Examiner* — Tatyana Zalukaeva
*Assistant Examiner* — Ginger T Chapman
(74) *Attorney, Agent, or Firm* — Volpe and Koenig, P.C.

(57) ABSTRACT

A method and device may be used to avoid surgically re-opening a stoma or the like in an animal, including human beings. The stoma stabilitating device comprises an anchoring portion, preferably flat, that includes an opening configured to surround a stoma. The anchoring portion preferably includes an inner tension ring attached to an inner edge to define the opening and a tension ring attached to an outer edge. The anchoring portion may include additional structural rings. The device may be of a mesh construction and used to maintain, for example, a stoma, a fistula, a tracheotomy and any other pathway from outside the body to the inner part of the body. The device may be used to maintain an open pathway for air and to maneuver devices within a cavity. The device may also be used internally.

20 Claims, 3 Drawing Sheets

U.S. PATENT DOCUMENTS

| Patent No. | Type | Date | Inventor(s) | Ref |
|---|---|---|---|---|
| 5,180,715 | A | 1/1993 | Parsons | |
| 5,269,774 | A * | 12/1993 | Gray | 604/343 |
| 5,301,688 | A | 4/1994 | Stephen et al. | |
| 5,352,183 | A | 10/1994 | Jonsson et al. | |
| 5,366,460 | A * | 11/1994 | Eberbach | 606/151 |
| 5,366,478 | A * | 11/1994 | Brinkerhoff et al. | 606/213 |
| 5,454,790 | A | 10/1995 | Dubrul | |
| 5,645,860 | A | 7/1997 | Knapp, Jr. et al. | |
| 5,762,966 | A | 6/1998 | Knapp, Jr. et al. | |
| 5,804,185 | A | 9/1998 | Bandman et al. | |
| 5,817,480 | A | 10/1998 | Murry et al. | |
| 5,843,472 | A | 12/1998 | Ma et al. | |
| 5,869,259 | A | 2/1999 | Hillman et al. | |
| 5,880,108 | A | 3/1999 | Morales et al. | |
| 5,888,986 | A | 3/1999 | Morales et al. | |
| 5,904,703 | A * | 5/1999 | Gilson | 606/213 |
| 5,954,767 | A * | 9/1999 | Pajotin et al. | 623/23.72 |
| 5,962,645 | A | 10/1999 | Keay et al. | |
| 5,998,373 | A | 12/1999 | Hillman et al. | |
| 6,017,355 | A * | 1/2000 | Hessel et al. | 606/184 |
| 6,063,596 | A | 5/2000 | Lal et al. | |
| 6,087,108 | A | 7/2000 | Bandman et al. | |
| 6,143,300 | A | 11/2000 | Stevenot | |
| 6,146,396 | A | 11/2000 | Kónya et al. | |
| 6,171,344 | B1 | 1/2001 | Atala | |
| 6,193,752 | B1 | 2/2001 | Hildebrandt | |
| 6,227,202 | B1 | 5/2001 | Matapurkar | |
| 6,242,179 | B1 | 6/2001 | Shah et al. | |
| 6,254,570 | B1 | 7/2001 | Rutner et al. | |
| 6,296,847 | B1 | 10/2001 | Gokcen et al. | |
| 6,332,892 | B1 | 12/2001 | Desmond, III et al. | |
| 6,360,750 | B1 | 3/2002 | Gerber et al. | |
| 6,364,868 | B1 | 4/2002 | Ikeguchi | |
| 6,368,338 | B1 | 4/2002 | Kónya et al. | |
| 6,371,992 | B1 | 4/2002 | Tanagho et al. | |
| 6,393,323 | B1 | 5/2002 | Sawan et al. | |
| 6,500,938 | B1 | 12/2002 | Au-Young et al. | |
| 6,589,277 | B1 * | 7/2003 | Fabiani et al. | 623/1.31 |
| 6,616,675 | B1 * | 9/2003 | Evard et al. | 606/155 |
| 6,620,202 | B2 | 9/2003 | Bottcher et al. | |
| 6,656,146 | B1 | 12/2003 | Clayman et al. | |
| 6,669,735 | B1 * | 12/2003 | Pelissier | 623/23.74 |
| 6,676,623 | B2 | 1/2004 | Whitmore, III | |
| 6,719,804 | B2 | 4/2004 | St. Pierre | |
| 6,849,069 | B1 | 2/2005 | Clayman et al. | |
| 6,863,892 | B2 | 3/2005 | Faris et al. | |
| 6,878,110 | B2 | 4/2005 | Yang et al. | |
| 6,898,454 | B2 | 5/2005 | Atalar et al. | |
| 6,911,003 | B2 | 6/2005 | Anderson et al. | |
| 6,945,950 | B2 | 9/2005 | Clayman et al. | |
| 6,991,614 | B2 | 1/2006 | McWeeney et al. | |
| 6,994,717 | B2 | 2/2006 | Kónya et al. | |
| 6,998,232 | B1 | 2/2006 | Feinstein et al. | |
| 7,037,345 | B2 | 5/2006 | Bottcher et al. | |
| 7,067,130 | B2 | 6/2006 | Challita-Eid et al. | |
| 7,070,556 | B2 | 7/2006 | Anderson et al. | |
| 7,087,041 | B2 * | 8/2006 | von Dyck et al. | 604/332 |
| 7,115,727 | B2 | 10/2006 | Faris et al. | |
| 7,122,362 | B2 | 10/2006 | Baughn et al. | |
| 7,131,996 | B2 | 11/2006 | Wasserman et al. | |
| 7,135,549 | B1 | 11/2006 | Challita-Eid et al. | |
| 7,182,745 | B2 | 2/2007 | Desmond et al. | |
| 7,208,280 | B2 | 4/2007 | Jakobovits et al. | |
| D543,626 | S | 5/2007 | Watschke et al. | |
| 7,217,237 | B2 | 5/2007 | Wasserman et al. | |
| 7,217,799 | B2 | 5/2007 | Raitano et al. | |
| 7,223,404 | B2 | 5/2007 | Cheung | |
| 7,226,594 | B2 | 6/2007 | Jakobovits et al. | |
| 7,244,827 | B2 | 7/2007 | Raitano et al. | |
| 7,250,498 | B2 | 7/2007 | Challita-Eid et al. | |
| 7,279,556 | B2 | 10/2007 | Challita-Eid et al. | |
| 7,291,180 | B2 | 11/2007 | St. Pierre | |
| 7,306,627 | B2 | 12/2007 | Tanagho et al. | |
| 7,308,412 | B2 | 12/2007 | Rakshit et al. | |
| 7,347,812 | B2 | 3/2008 | Mellier | |
| 7,351,197 | B2 | 4/2008 | Montpetit et al. | |
| 7,357,773 | B2 | 4/2008 | Watschke | |
| 7,358,353 | B2 | 4/2008 | Jakobovits et al. | |
| 7,361,338 | B2 | 4/2008 | Jakobovits et al. | |
| 7,377,898 | B2 * | 5/2008 | Ewers et al. | 600/208 |
| 7,405,290 | B2 | 7/2008 | Challita-Eid et al. | |
| 7,410,477 | B2 * | 8/2008 | Gomez | 604/96.01 |
| 7,427,399 | B2 | 9/2008 | Jakobovits et al. | |
| 7,427,619 | B2 | 9/2008 | Burzynski | |
| 7,431,701 | B2 | 10/2008 | Schmidt | |
| 7,449,548 | B2 | 11/2008 | Raitano et al. | |
| 7,459,539 | B2 | 12/2008 | Challita-Eid et al. | |
| 7,479,161 | B1 | 1/2009 | Wassermann et al. | |
| 7,488,479 | B2 | 2/2009 | Faris et al. | |
| 7,494,646 | B2 | 2/2009 | Challita-Eid et al. | |
| 7,500,945 | B2 | 3/2009 | Cox et al. | |
| 7,501,502 | B2 | 3/2009 | Raitano et al. | |
| 7,504,387 | B2 | 3/2009 | Marcum | |
| 7,510,840 | B1 | 3/2009 | Challita-Eid et al. | |
| 7,519,429 | B2 | 4/2009 | Sawan et al. | |
| 7,541,442 | B2 | 6/2009 | Gudas et al. | |
| 7,553,814 | B2 | 6/2009 | Raitano et al. | |
| 7,563,444 | B2 | 7/2009 | Challita-Eid et al. | |
| 7,585,505 | B2 | 9/2009 | Challita-Eid et al. | |
| 7,592,149 | B2 | 9/2009 | Challita-Eid et al. | |
| 7,595,379 | B2 | 9/2009 | Gudas et al. | |
| 7,599,729 | B2 | 10/2009 | Atalar et al. | |
| 7,601,825 | B2 | 10/2009 | Challita-Eid et al. | |
| 7,608,704 | B2 | 10/2009 | Yue et al. | |
| 7,612,172 | B2 | 11/2009 | Faris et al. | |
| 7,615,379 | B2 | 11/2009 | Raitano et al. | |
| 7,622,564 | B2 | 11/2009 | Ge et al. | |
| 7,622,569 | B2 | 11/2009 | Raitano et al. | |
| 7,628,989 | B2 | 12/2009 | Jakobovits et al. | |
| 7,638,270 | B2 | 12/2009 | Kanner et al. | |
| 7,641,905 | B2 | 1/2010 | Jakobovits et al. | |
| 7,642,342 | B2 | 1/2010 | Challita-Eid et al. | |
| 7,655,234 | B2 | 2/2010 | Challita-Eid et al. | |
| 7,659,377 | B2 | 2/2010 | Raitano et al. | |
| 7,666,133 | B2 | 2/2010 | Drager | |
| 7,667,015 | B2 | 2/2010 | Challita-Eid et al. | |
| 7,667,018 | B2 | 2/2010 | Jakobovits et al. | |
| 7,828,854 | B2 * | 11/2010 | Rousseau et al. | 623/23.72 |
| 7,867,164 | B2 * | 1/2011 | Butler et al. | 600/208 |
| 7,951,076 | B2 * | 5/2011 | Hart et al. | 600/206 |
| 8,105,234 | B2 * | 1/2012 | Ewers et al. | 600/208 |
| 8,142,354 | B1 * | 3/2012 | Larson et al. | 600/203 |
| 8,172,749 | B2 * | 5/2012 | Melsheimer | 600/184 |
| 2003/0171823 | A1 | 9/2003 | Zotti et al. | |
| 2003/0212460 | A1 | 11/2003 | Darois et al. | |
| 2004/0260153 | A1 * | 12/2004 | Pulford et al. | 600/208 |
| 2005/0277946 | A1 * | 12/2005 | Greenhalgh | 606/108 |
| 2006/0149306 | A1 * | 7/2006 | Hart et al. | 606/191 |
| 2007/0179426 | A1 | 8/2007 | Selden | |
| 2008/0269698 | A1 * | 10/2008 | Alexander et al. | 604/332 |
| 2009/0192464 | A1 | 7/2009 | Axelsson et al. | |
| 2009/0299388 | A1 * | 12/2009 | Barker et al. | 606/155 |
| 2011/0015475 | A1 * | 1/2011 | Hanuka et al. | 600/32 |
| 2011/0092929 | A1 * | 4/2011 | Weig | 604/338 |

* cited by examiner

STOMA STABILITATING DEVICE AND METHOD

TECHNOLOGY FIELD

This application is related to medical devices and methods.

BACKGROUND

A stoma may be surgically created in various situations in the treatment of an animal, including human beings. For example, a stoma may be surgically created to remove urine from a patient who may have had their bladder removed. Over time, such a stoma may constrict or close completely, causing urine to backup in the kidneys. A typical solution to stoma closure or restriction is to surgically re-open the stoma. Performing repeated surgeries on the same area may cause serious complications, scarring and patient discomfort. It would therefore be desirable to have a method and device to avoid surgically re-opening stomas.

SUMMARY

A stoma stabilitating devices and methods are disclosed. The stoma stabilitating device comprises an anchoring portion, preferably flat, that includes an opening configured to surround a stoma. The anchoring portion preferably includes an inner tension ring attached to an inner edge to define the opening and a tension ring attached to an outer edge. The anchoring portion may include structural rings. The stoma stabilitating device may include one or more tubular extensions extending from the anchoring portion opening. The tubular extensions may be attached to the anchoring portion at any angle and at any rotational orientation. The stoma stabilitating device may be constructed using a knitted or woven mesh or any other suitable material.

The stoma stabilitating device is preferably used to avoid surgically re-opening a stoma. The stoma stabilitating device may be used to stabilize, for example, a stoma, a fistula, a tracheotomy and any other pathway from outside the body to the inner part of the body, and/or to connect two or more body cavities or structures. The stoma stabilitating device may be used to maintain an open pathway for air and to maneuver devices within a cavity. The stoma stabilitating device may also be used internally as an anchor for various purposes.

BRIEF DESCRIPTION OF THE DRAWINGS

A more detailed understanding may be had from the following description, given by way of example in conjunction with the accompanying drawings wherein.

DETAILED DESCRIPTION

Figure 1:
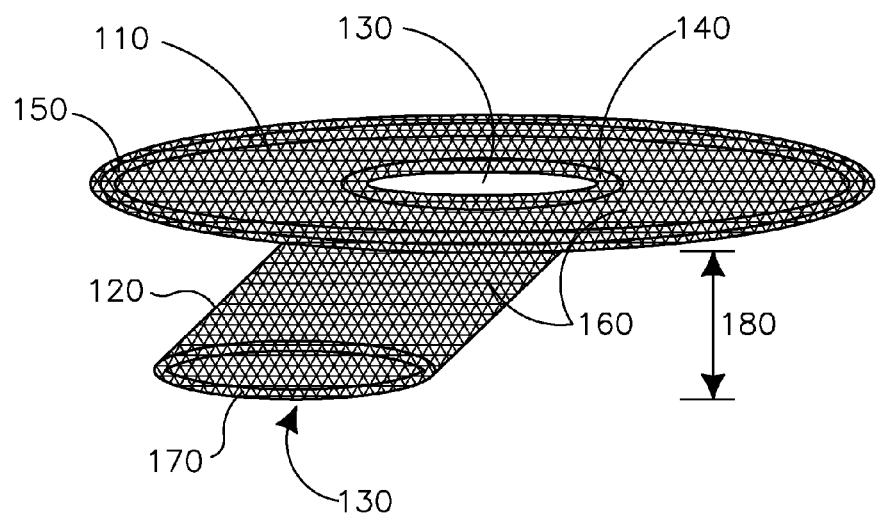
FIG. 1 is a diagram of an example stoma stabilitating device.

Various embodiments are described herein where like reference numerals are used to describe like features. Each feature or element may be used alone without the other features and elements or in various combinations with or without other features and elements.

A stoma stabilitating device may aid in stabilizing, for example, a stoma, a fistula, a tracheotomy and any other pathway from outside the body to the inner part of the body, and/or to join two or more body cavities or structures. The stoma stabilitating device may be used for an opening to remove bodily fluids, for example in an Ileostomy/Urostomy scenario. Alternatively, the stoma stabilitating device may be used to aid removal of solids from the body, for example in a Colostomy scenario. In yet another alternative, the stoma stabilitating device may be used to maintain an open pathway for air and to maneuver devices within a cavity. The stoma stabilitating device may also be used internally as an anchor for various purposes, such as when two structures may be adjoined by a fistula. One example may be for use in a ureterocolic diversion such that urine may be diverted into the colon. The stoma stabilitating device may be incorporated into the portal section of a man made opening, for example a surgical defect and/or a pathway that may allow liquids or solids to pass bidirectionally.

The stoma stabilitating device may be applied subcutaneously (sub-Q), intramuscularly, interperitoneumly, and/or to join two or more body cavities or structures. The stoma stabilitating device may be constructed with fibers and rings that may be absorbable or non-absorbable, for example the stoma stabilitating device may be constructed using materials such as, for example, Polydioxanone (PDO) and/or stainless steel. The stoma stabilitating device may incorporate a matrix configured to stabilize a stoma or other opening while allowing new tissue in-growth within its fibers and rings. The matrix may be made of natural and/or synthetic materials that are biodegradable, fully degradable, partially degradable, and/or non degradable, such that the matrix may or may not be absorbed by the body.

The matrix may be formed into a mesh or any other suitable configuration. For simplicity, the matrix may be referred to as a mesh by way of example and may be any other suitable configuration. The mesh may be constructed with many different materials and with many different patterns. For example, the matrix may be constructed from an extrudable non-absorbable monofilament polypropylene and knitted or woven in various mesh configurations. Other example matrices may include, but are not limited to PDO, polyester (PET), polytetrafluoroethylene (PTFE), and/or polyethylene (PE). Although the examples disclosed in detail below have a mesh construction, other suitable material can be employed for the construction of the stoma stabilitating device.

The stoma stabilitating device includes an anchoring portion that defines an opening and may be configured in any shape, preferably with a centrally located opening or cutout, but the opening location is not limited to a central location within the anchoring portion. The anchoring portion is preferably substantially flat and is preferably designed to be maintained in a substantially flat orientation when it is attached to an animal in use. In this context, substantially flat includes being contoured to conform with the portion of a body to which the stoma stabilitating device is anchored.

An outer edge of the stoma stabilitating device and an inner opening defining edge may be reinforced with a PDO monofilament material fashioned in a hoop, ring or flat in the shape of a washer. In one configuration, the stoma stabilitating device may comprise a circle of knitted or woven material with a circular cutout in the center. The stoma stabilitating device may be implanted sub-Q and centered on a stoma opening. The stoma stabilitating device may be used to maintain a stoma to reduce the risk of stoma stenosis failure.

FIG. 1 is a diagram of an example stoma stabilitating device 100. The stoma stabilitating device 100 includes a substantially flat anchoring portion 110 having an opening 130 and a tubular extension 120 extending at a desired angle therefrom. The anchoring portion 110 and the tubular extension 120 are preferably constructed from mesh material 160. The angle between the anchoring portion 110 and the tubular extension 120 is preferably between 0 and 90 degrees depending on the intended use of the stoma stabilitating device including the size and shape of the stoma or other opening that is to be stabilized. The opening 130 may be circular, oval, or any other suitable shape to adapt to the contour of the tissue that is used to make the stoma that is to be stabilized.

The stoma stabilitating device 100 is preferably implanted such that the opening 130 is placed over the stoma site. In sub-Q stoma applications, the stoma stabilitating device 100 is preferably anchored around a stoma between the skin and muscles with the extension 120 extending into the stoma. However, the extension 120 may extend away from the stoma in some applications.

The anchoring portion 110 includes an inner washer shaped tension ring 140 about the opening 130 and an outer tension ring 150 that provides a desired amount of tension to the anchoring portion mesh. The inner tension ring 140 may assist in preventing tissue from contracting or encroaching inwards towards the stoma site, thereby allowing the stoma site to remain open. The outer tension ring 150 is preferably configured such that the anchoring portion 10 remains substantially flat while implanted. The outer tension ring 150 may also be used as tacking points for sutures and anchors to tissue. Preferably the outer tension ring 150 defines an outer edge of the anchoring portion 110. Preferably the outer tension ring 150 is substantially concentric with the inner tension ring 140. The inner tension ring 140 and outer tension ring 150 preferably have a thickness of 0.25 mm to 2 mm, however the thickness may vary outside this range based on patient variability, type of application, type of material, or other variables. In one example, the inner tension ring 140 and the outer tension ring 150 have a thickness of 1 mm. In certain applications, it may be advantageous to not have an inner tension ring 140 and/or an outer tension ring 150.

The outer tension ring 150 may be circular, oval, or any other suitable shape based on the size of the patient and anatomical variation. The outer tension ring 150 is generally approximately 20 mm to 300 mm in diameter based on patient variation and device application, but preferably in the range of 90 mm to 100 mm. The inner tension ring 140 and opening 130 preferably have a diameter generally approximately 45 mm, however these diameters may be varied based on patient variation and device application. Radial tension may be applied in addition to or instead of the inner tension ring 140 and/or the outer tension ring 150, for example, by using a wheel-and-spoke type configuration (not shown) or any other suitable configuration.

The mesh material 160 may be constructed from various materials including, but not limited to, Monofilament Polypropylene. The mesh 160 may support tissue in-growth and have various perforations, stiffness and flexibility properties. Tissue contraction and inward encroachment towards the stoma may be prevented by allowing tissue in-growth through the mesh 160. The open knit pattern or weave may encourage tissue in-growth. For example, the stiffness of the mesh 160 may maintain a flat surface to allow for uniform tissue in-growth, whereas flexibility of the mesh 160 may allow the stoma stabilitating device 100 to conform to the natural body contour and aid in patient comfort. The stoma stabilitating device 100 may provide stability to the passing tissue (stoma, diversion, etc.) until tissue in-growth has occurred, which may stabilize and minimize the amount of tissue contraction at the application site. The mesh 160 may be constructed in a single or a multiple layer configuration. The mesh 160 may allow flat tissue integration, for example, in sub-Q, dermal, fascia, muscle and peritoneum applications. This integration may create opposing forces across the planar surface of the mesh 160 that may prevent contraction or expansion of the stoma.

The tubular extension 120 may include a support ring 170 to assist in maintaining the opening 130 substantially fully open through the tubular extension. The diameter of the support ring 170 may be varied based on the anatomical size and shape of the stoma formation and patient variability. The support ring 170 may have a diameter between 2 mm and 80 mm, however this general range may be extended based on the patient and stoma opening variability. The length 180 of the tubular extension 120 may be between 0 mm and 80 mm from the anchoring portion 110 to the end of the tubular extension 120. The extension dimension 180 of the tubular extension 120 from the anchoring portion 120 is preferably determined based on patient and stoma opening variability. The tubular extension 120 may be constructed with the same mesh 160 as the anchoring portion 110, or it may be constructed with a different mesh with different properties based on the application. The tubular extension 120 may be implanted onto the muscle, below the skin. In one example, the tubular extension 120 is implanted onto or within the muscle when the stoma stabilitating device is in use.

Figure 2:
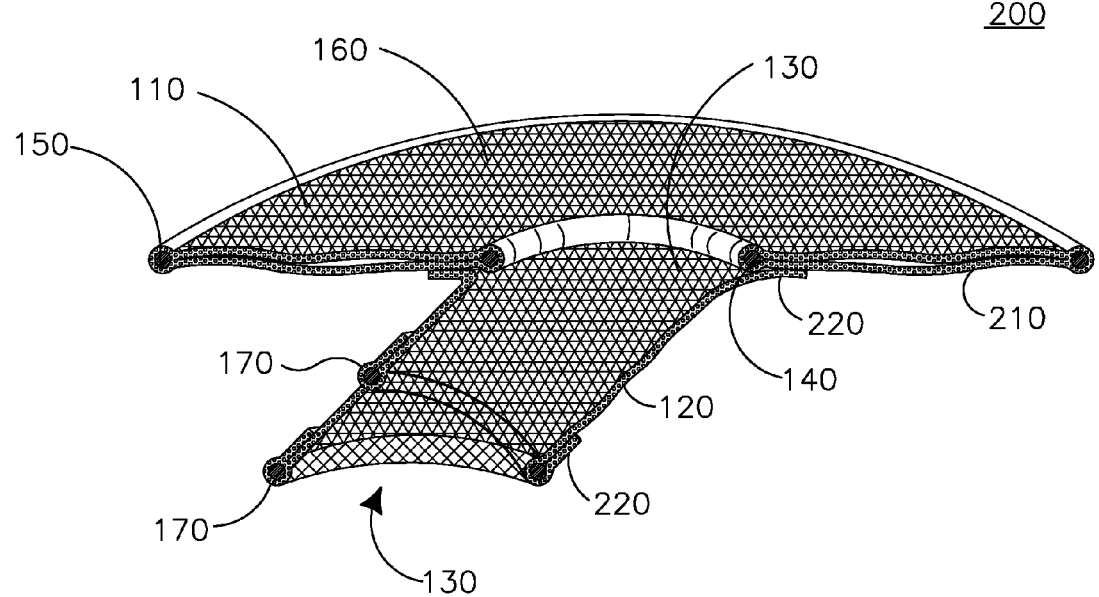
FIG. 2 is a cross-section diagram of a variation of the stoma stabilitating device shown in FIG. 1 with a multiple layer configuration.

FIG. 2 is a cross-section diagram of a variation of the stoma stabilitating device shown in FIG. 1 with a multiple layer configuration. The multiple layer configuration is preferably constructed by using two or more layers of mesh 160 for the anchoring portion 110 to increase rigidity. The layers may be loosely bound or sown, adhered together with medical adhesive, and/or ultrasonically or thermally welded together. Referring to FIG. 2, the anchoring portion 110 of the stoma stabilitating device 200 is constructed as a double layer configuration 210 with the mesh material wrapping around outer and inner tension rings 150, 140 that are made of suitable monfilament. In the FIG. 2 example, the tubular extension 120 is illustrated as having an open end defined by support ring 170. Two alternative orientations of the open end of the tubular extension 120 are illustrated in FIG. 2, one where the support ring 170 defining the end is substantially parallel to the anchoring portion 110 and the other where the support ring 170 defining the end is at a substantial angle relative to the anchoring portion 110.

Additional structural or tension rings (not shown) may be used to increase the strength and rigidity of the mesh 160. Such structural rings may be added in the anchoring portion 110 between the inner tension ring 140 and the outer tension ring 150 or in the tubular extension 120 for additional strength and/or rigidity. The additional rings may also be used for tacking sutures. The structural or tension rings may be made of various materials, including but not limited to PDO. Where multiple mesh layers are provided, they may be fused together to prevent the rings from moving, contracting or expanding.

Figure 3:
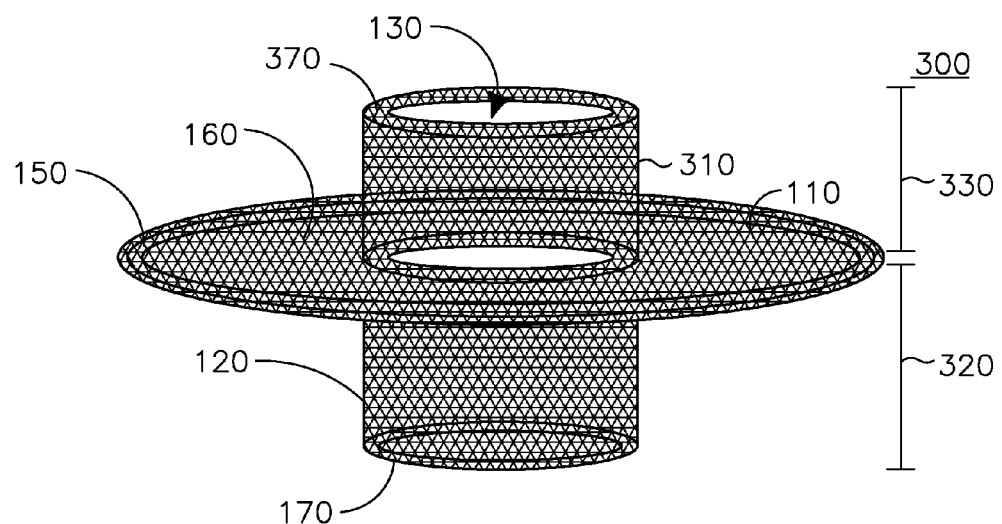
FIG. 3 is a diagram of an example stoma stabilitating device.

FIG. 3 illustrates another example stoma stabilitating device. As shown in FIG. 3, the stoma stabilitating device 300 includes a substantially flat anchoring portion 110, a first tubular extension 120, and a second tubular extension 310. The anchoring portion 110 defines an opening 130 that also extends through the tubular extensions 120, 310. The anchoring portion 110 includes an inner tension ring 140 and an outer tension ring 150 and is preferably constructed from mesh material 160.

The first tubular extension 120 and the second tubular mesh 310 may be constructed of the same mesh material or of a different material depending upon application and may be configured as a singular tubular extension extending through the anchoring portion 110. The first tubular extension 120 and the second tubular extension 310 preferably each include a support ring 170, 370, respectively, to assist in maintaining opening 130 substantially fully open. The extension dimension 320 of the first tubular extension 120 from the anchoring portion 110 may either be the same or different than the extension dimension 330 of the second tubular extension 310 from the anchoring portion 110.

The first tubular extension 120 and the second tubular extension 310 extend orthogonally from the anchoring portion 110 in the example illustrated in FIG. 3. However, either or both of the tubular extensions 120, 310 may extend at a non-orthogonal angle from the anchoring portion 110. The angle of extension of the first tubular extension 120 may differ from the angle of extension of the second tubular extension 310.

Figure 4:
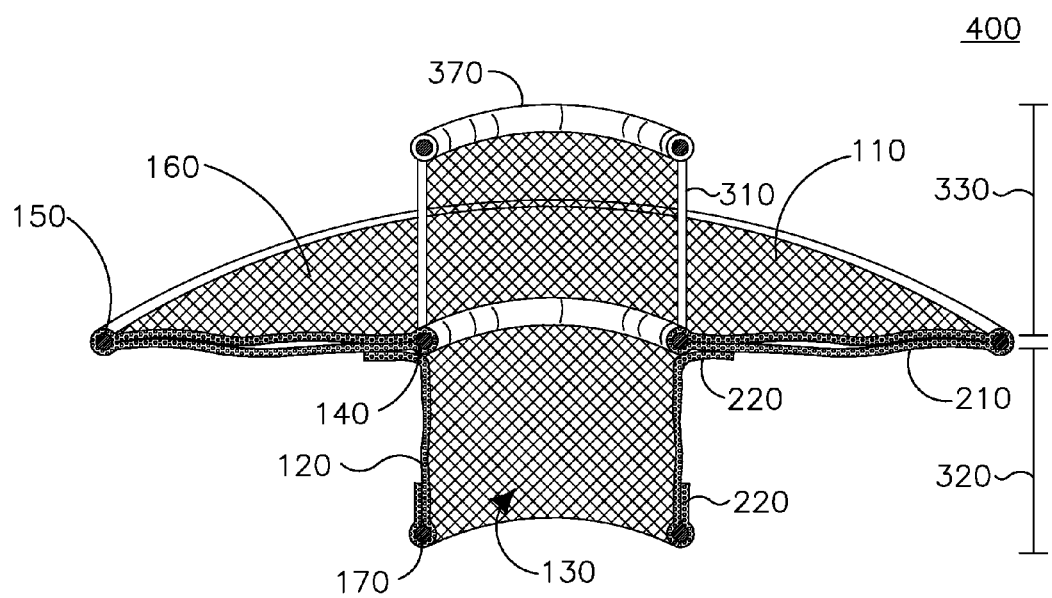
FIG. 4 is a cross-section diagram of a variation of the stoma stabilitating device shown in FIG. 3 with a multiple layer configuration.

FIG. 4 is a cross-section diagram of a variation of the stoma stabilitating device shown in FIG. 3 with a multiple layer mesh configuration. Multiple layer configurations may be constructed by using two or more layers of mesh 160 for the anchoring portion 110 to increase rigidity. The layers may be loosely bound or sown, adhered with medical adhesive, and/or ultrasonically or thermally welded together.

Referring to the FIG. 4 example, the anchoring portion 110 of the stoma stabilitating device 400 is constructed as a double layer configuration 210. First tubular extension 120 and second tubular extension 310 are attached to the anchoring portion 110 at the inner tension ring 140 to define the opening 130 that extends through the anchoring portion 110 and the extensions 120, 310. Tension and support rings 140, 150, 170, 370 are provided as in the prior example. In the FIG. 4 example, the rings 140, 150, 170, 370 are maintained in position by having mesh material wrapped around themselves. Additional structural or tension rings (not shown) may be used to increase the strength and rigidity of the anchoring portion 110 and the extensions 120, 310.

Figure 5:
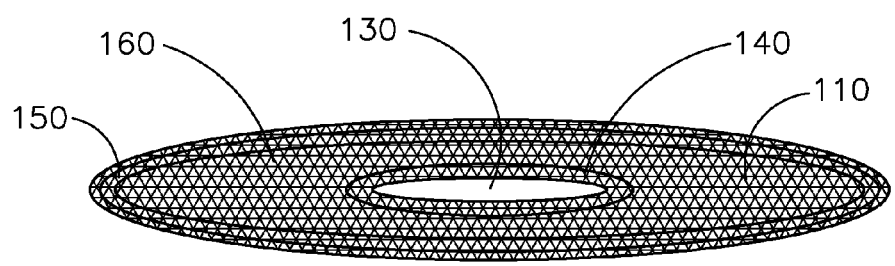
FIG. 5 is a diagram of an example stoma stabilitating device.

FIG. 5 illustrates a further example of a stoma stabilitating device 500 that does not include a tubular extension. Referring to FIG. 5, the stoma stabilitating device 500 has a substantially flat anchoring portion 110, preferably constructed out of mesh material 160. The anchoring portion 110 includes an inner washer shaped tension ring 140 that defines an opening 130 and an outer tension ring 150. Preferably the outer tension ring 150 defines an outer edge of the anchoring portion 110. Preferably the outer tension ring 150 is substantially concentric with the inner tension ring 140. The stoma stabilitating device 500 is preferably implanted such that the opening 130 is located over a stoma or other opening and anchored into place by attaching the anchoring portion via suturing or other suitable means. The opening 130 may be circular, oval, or any other suitable shape to adapt to the contour of the tissue that is used to make the stoma. The inner tension ring 140 prevents tissue from contracting or encroaching inwards towards the stoma site, thereby allowing the stoma to remain substantially fully open. The outer tension ring 150 is preferably configured such that the anchoring portion is maintained in a relatively flat orientation while in use. The outer tension ring 150 may also be used as tacking points for sutures and anchors to tissue. The rings 140, 150 may be circular, oval, or any other suitable shape based on the size of the patient and anatomical variation. The outer tension ring 150 is preferably approximately 10 mm to 300 mm in diameter based on patient variation and device application.

The mesh 160 may be constructed from various materials including, but not limited to, Monofilament Polypropylene. The mesh 160 may support tissue in-growth and have various perforations, stiffness and flexibility properties, as described above. Tissue contraction and inward encroachment towards the stoma may be prevented by allowing tissue in-growth through the mesh 160. The stoma stabilitating device 500 may provide stability to the passing tissue (stoma, diversion, etc.) until tissue in-growth has occurred, and may stabilize and/or minimize the amount of tissue contraction at the application site. The mesh 160 may be constructed in a single or multiple layer configuration. The mesh 160 may allow flat tissue integration, for example, in sub-Q, dermal, fascia, muscle and peritoneum applications. This integration may create opposing forces across the planar surface of the mesh 160 that may prevent constriction or expansion of the stoma.

Figure 6:
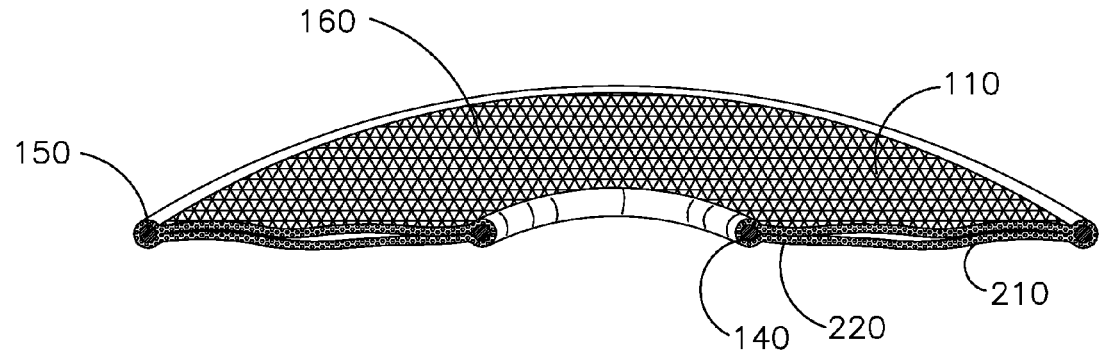
FIG. 6 is a cross-section diagram of a variation of the stoma stabilitating device shown in FIG. 5 with a multiple layer configuration.

FIG. 6 illustrates a variation of the example stoma stabilitating device shown in FIG. 5, but with a multiple layer configuration. The multiple layer configuration may be constructed by using two or more layers of mesh 160 to increase rigidity. The layers may be loosely bound or sown, adhered with medical adhesive, and/or ultrasonically or thermally welded together.

Referring to the FIG. 6 example, the stoma stabilitating device 600 is has an anchoring portion 110 constructed with a double layer mesh 210 and including inner and outer rings 140, 150. Additional structural or tension rings (not shown) may be used to increase the strength and rigidity of the anchoring portion 110. Such rings may be added anywhere in the anchoring portion 110 between the inner tension ring 140 and the outer tension ring 150. The structural rings may be added between the mesh layers 210 and/or interwoven within the mesh 160. Mesh layers may be fused together to prevent any structural or tension rings from contracting or expanding. The structural or tension rings may be made of various materials, including but not limited to PDO.

Although features and elements are described above in particular combinations, each feature or element can be used alone without the other features and elements or in various combinations with or without other features and elements.

What is claimed is:

1. A stoma stabilitating device comprising:
   a substantially flat anchoring portion including an inner tension ring defining an opening configured to surround a stoma or the like, wherein the stoma stabilitating device maintains the stoma or the like such that the stoma or the like remains open;
   wherein the anchoring portion constructed of a material suitable for implantation into a living animal and configured to maintain a substantially flat orientation with the inner tension ring in a substantially fully open orientation when in use;
   wherein the anchoring portion is constructed of a mesh material and includes an outer tension ring to provide tension to the mesh material of the anchoring portion disposed between the inner and outer rings such that the mesh material is maintained in a substantially fully open orientation; and
   a tubular extension extending from one side of the anchoring portion at the opening, wherein the tubular extension is constructed of a mesh material, has one end attached to the anchoring portion and a second end that includes a support ring to maintain the opening defined by the anchoring portion substantially fully opened through the tubular extension.

2. The stoma stabilitating device of claim 1 wherein the outer tension ring defines an outer edge of the anchoring portion and is substantially concentric with the inner tension ring.

3. The stoma stabilitating device of claim 2 wherein the outer tension ring has a diameter between 1 cm and 25 cm.

4. The stoma stabilitating device of claim 3, wherein the inner tension ring has a diameter between 0.5 cm and 8 cm.

5. The stoma stabilitating device of claim 1 wherein the anchoring portion comprises two mesh layers welded together at outer and inner edges.

6. The stoma stabilitating device of claim 5 wherein the rings are polydioxanone (PDO) monofilament rings.

7. The stoma stabilitating device of claim 6 wherein the PDO monofilament rings are a circular shape.

8. The stoma stabilitating device of claim 6 wherein the rings comprise washers welded between the two mesh layers.

9. The stoma stabilitating device of claim 1 wherein the outer tension ring defines an outer edge of the anchoring portion and is substantially concentric with the inner tension ring.

10. The stoma stabilitating device of claim 1 further comprising:
    a second tubular extension extending from an opposite side of the anchoring portion at the opening.

11. The stoma stabilitating device of claim 10 wherein the tubular extensions are constructed of a mesh material and each tubular extension has one end attached to the anchoring portion and a second end that includes a support ring to maintain the opening defined by the anchoring portion substantially fully opened through the tubular extension.

12. The stoma stabilitating device of claim 11 wherein the outer tension ring defines an outer edge of the anchoring portion and is substantially concentric with the inner tension ring.

13. A stoma stabilitating device comprising:
    a substantially flat anchoring portion including an inner tension ring defining an opening configured to surround a stoma or the like, wherein the stoma stabilitating device maintains the stoma or the like such that the stoma or the like remains open;
    wherein the anchoring portion constructed of a material suitable for implantation into a living animal and configured to maintain a substantially flat orientation with the inner tension ring in a substantially fully open orientation when in use;
    wherein the anchoring portion is constructed of a mesh material and includes an outer tension ring to provide tension to the mesh material of the anchoring portion disposed between the inner and outer rings such that the mesh material is maintained in a substantially fully open orientation, and wherein the outer tension ring defines a substantially continuous outer edge of the anchoring portion.

14. The stoma stabilitating device of claim 13 wherein the outer tension ring defines an outer edge of the anchoring portion and is substantially concentric with the inner tension ring.

15. The stoma stabilitating device of claim 14 wherein the outer tension ring has a diameter between 1 cm and 25 cm.

16. The stoma stabilitating device of claim 15, wherein the inner tension ring has a diameter between 0.5 cm and 8 cm.

17. The stoma stabilitating device of claim 13 wherein the anchoring portion comprises two mesh layers welded together at outer and inner edges.

18. The stoma stabilitating device of claim 17 wherein the rings are polydioxanone (PDO) monofilament rings.

19. The stoma stabilitating device of claim 18 wherein the PDO monofilament rings are a circular shape.

20. The stoma stabilitating device of claim 17 wherein the rings comprise washers welded between the two mesh layers.

\* \* \* \* \*